United States Patent [19]
Nelson et al.

[11] Patent Number: 5,934,997
[45] Date of Patent: Aug. 10, 1999

[54] METHOD OF DETERMINING THE MOISTURE CONTENT OF GRAIN

[75] Inventors: George F. Nelson, Coon Rapids; Ray E. Artz; Paul A. Leavitt, both of Apple Valley, all of Minn.

[73] Assignee: New Holland North America, Inc., New Holland, Pa.

[21] Appl. No.: 09/168,219

[22] Filed: Oct. 8, 1998

Related U.S. Application Data

[63] Continuation of application No. 08/917,481, Aug. 26, 1997, Pat. No. 5,871,397.

[51] Int. Cl.$^6$ ..................................................... A01F 12/00
[52] U.S. Cl. ........................... 460/7; 460/149; 56/10.2 B; 56/DIG. 15
[58] Field of Search ................................... 460/7, 1, 114, 460/119, 149, 150; 56/10.2 B, DIG. 15

[56] References Cited

U.S. PATENT DOCUMENTS

| | | | |
|---|---|---|---|
| 5,092,819 | 3/1992 | Schroeder et al. | 460/7 |
| 5,106,339 | 4/1992 | Braun et al. | 460/7 |
| 5,480,354 | 1/1996 | Sadjadi | 56/10.2 B X |
| 5,685,772 | 11/1997 | Anderson et al. | 460/7 X |
| 5,716,272 | 2/1998 | Nelson | 460/7 |

OTHER PUBLICATIONS

Microwave Monitoring Moisture Content in Grain–Further Consideration; International Microwave Power Institute; 1988; vol. 23 No. 4, 1988; pp. 236–246.

Use of a Density Indepenndent Function and Microwave Measuremen System for Grain Moisture Measurement 1988 Am. Society of Agricultural Eng.; vol. 31(6); Nov.–Dec. 1988.

Microwave Moisture Measurement of Grains; IEEE Transactions on Instrumentation and Measurement; vol. 41, No. 1, Feb. 1992; pp. 111–115.

Density–Independent Microwave Measurement of Moisture Content in Static and Flowing Grain; 1993 Am. Society of Agricultural Engineers; vol. 36(3) May –Jun.; pp. 827–835.

Microwave Sensors for Process Control Part I; Transmission Sensors; Ray J. King, KDC Technology Corp.; Sensors, Sep. 1992; pp. 68–74.

*Primary Examiner*—Terry Lee Melius
*Attorney, Agent, or Firm*—Griffin, Butler, Whisenhunt & Szipl, LLP

[57] ABSTRACT

A microwave grain monitor determines grain density and moisture content without measuring the phase shift of the measurement signal in passing through the grain. A set of grain coefficients is determined and stored in a non-volatile memory. A microwave measurement signal is transmitted through the grain and the ambient temperature is sensed. The grain density and moisture content are determined from the attenuation of the measurement signal in passing through the grain, the sensed temperature and the set of grain coefficients.

8 Claims, 2 Drawing Sheets

METHOD OF DETERMINING THE MOISTURE CONTENT OF GRAIN

RELATED APPLICATIONS

This application is a continuation of application Ser. No. 08/917,481, filed Aug. 26, 1997 now U.S. Pat. No. 5,871,397.

FIELD OF THE INVENTION

The present invention relates to grain monitors for measuring crop moisture and yield as a grain is being harvested by an agricultural harvesting machine. More particularly, the invention relates to a microwave moisture/yield monitor wherein the moisture content of the grain and the crop yield are determined without measurement of phase shift during the harvesting operation.

BACKGROUND OF THE INVENTION

The principle of microwave measurement of grain moisture and mass density has been very well described in technical papers produced by various researchers. Dr. S. O. Nelson and Dr. A. Kraszewski, USDA, Athens, Ga. have provided numerous papers explaining the theory and experimental proof of the validity of using attenuation and phase wave parameters to determine the moisture content and mass of selected grains. The experimental work has emphasized the need to measure both attenuation and phase shift in the grain since both are density dependent functions. This work has led to using ratios of these two density dependent parameters to eliminate the density dependence.

Density-independent techniques are critical when grain is flowing through a system which contains a measurement in a free-fall state. Free-fall is thought to provide a convenient means to move the grain through the measurement system without mechanical flow control apparatus being placed within the moisture/mass sensor, but free-fall introduces significant additional problems as detailed in "Density-independent Microwave Measurement of Moisture content in Static and Flowing Grain", B. D. McLendon, B. G. Branch, S. A. Thompson, A. Kraszewski, S. O. Nelson, ASAE Vol. 36(3):827–835—May–June 1993. Free-fall particles are not uniformly distributed throughout the confined space they are falling through. They actually cluster in changing geometrical patterns of varying densities. These clusters of particles then move around within the space because of the Magnus effect. In addition, the velocity of the falling particles varies in both the location of the particle relative to the wall of the confining space and between and within the clusters described above. When the grain falls it also accelerates through the sensor so the speed of the grain is increasing while the bulk density is decreasing in the vicinity of the RF measurement. All these variables are difficult to quantify and cause additional errors in the mass/moisture measurement.

It can be seen that if the attenuation measurement is to have meaning, the relative bulk density of the material being measured must simultaneously be determined. This measurement of the wave parameters, normalized to the bulk density, results in a meaningful measurement with the capability of providing an indication of the moisture content of the grain under test. Attempts to control the flow bulk density are discussed in the paper referenced above. A container of grain is placed above a controlled orifice and the grain is allowed to flow through the orifice in a slow controlled manner. This does reduce the increasing aeration of the grain while flowing, but it introduces another difficulty in that the grain is flowing in a small stream in the core of the container and another distribution in flow and bulk density occurs between the flowing grain core and the grain which is not flowing. In addition, this method is difficult to implement in the field while harvesting grain. The back-up of grain necessary before the flow restriction causes a significant decrease in the through-put of the harvester and presents a choke point or obstruction for the grain to jam in the machine sensor.

The copending application of George F. Nelson, Ser. No. 08/744,217, discloses a microwave grain monitor wherein grain is pushed upwardly, against gravity, through the grain tube of a harvesting machine by an auger, the grain tube extending through the microwave sensor region. This ensures that the bulk density of the grain is essentially constant, without a varying distribution of material bulk density through the sensor. Secondly, this ensures that the grain is fed into the sensor under positive flow conditions where all the grain can only move through the known cross-sectional area of the sensor. Under these conditions the wave parameters of phase and attenuation are not both needed to continuously measure the bulk density. We have determined that the effect of gravity and the grain particle shape causes the grain to always be packed to a density related to its moisture content hence measurement of the phase parameter is not required. Experiments in our laboratory have proven this to be true. The addition of the phase measurement increases the moisture and bulk density measurement accuracy only marginally, about 5.0% error versus 4.0% error.

SUMMARY OF THE INVENTION

An object of the present invention is to provide a method and apparatus for the microwave measurement of grain moisture content and/or crop yield during harvesting without direct measurement of the grain density during the harvesting operation.

Another object of the invention is to provide a method and apparatus for the microwave measurement of grain moisture content and/or crop yield without concurrent measurement of phase shift.

Yet another object of the invention is to provide a grain monitor for measuring the moisture content of grain as the grain is being harvested, the monitor comprising means for pushing the harvested grain through a tube extending through a sensing region, means for transmitting a microwave measurement signal through the sensing region, means for detecting the magnitude of the measurement signal after it has passed through the sensing region, and microprocessor means responsive to the detecting means for determining the moisture content of grain in the sensor region. The microprocessor includes a non-volatile memory storing sets of grain density coefficients, one set for each type of grain to be harvested. An operator control panel is used to select one set of coefficients prior to the time a harvesting operation is commenced. The microprocessor includes means, responsive to the detecting means, for first calculating the attenuation of the measurement signal in passing through the grain in the sensor region. After the attenuation has been calculated, the densities of wet matter (i.e. water) and dry matter within the grain are calculated using the calculated attenuation and the selected set of density coefficients. The moisture content and overall density is then calculated from the wet and dry densities.

A grain temperature sensor is provided for temperature correction during the calculation of moisture content. A Doppler transceiver may be provided for measuring the velocity of grain flow through the sensing region, thereby permitting microprocessor calculation of the volume and mass grain flow.

A further object of the invention is to provide a method of determining the moisture content and bulk density of grain as it is being harvested, the method comprising establishing a set of grain density coefficients for the type of grain to be harvested and storing the coefficients in a microprocessor memory, pushing harvested grain through a sensing region against gravity, measuring the attenuation of a microwave measurement signal in passing through grain in the sensing region, and calculating the bulk density and moisture content of the grain from the attenuation and the stored coefficients.

Other objects of the invention, its advantages, and the manner of making and using it will become obvious upon consideration of the following description and the accompanying drawings.

DESCRIPTION OF PREFERRED EMBODIMENT

Figure 1:
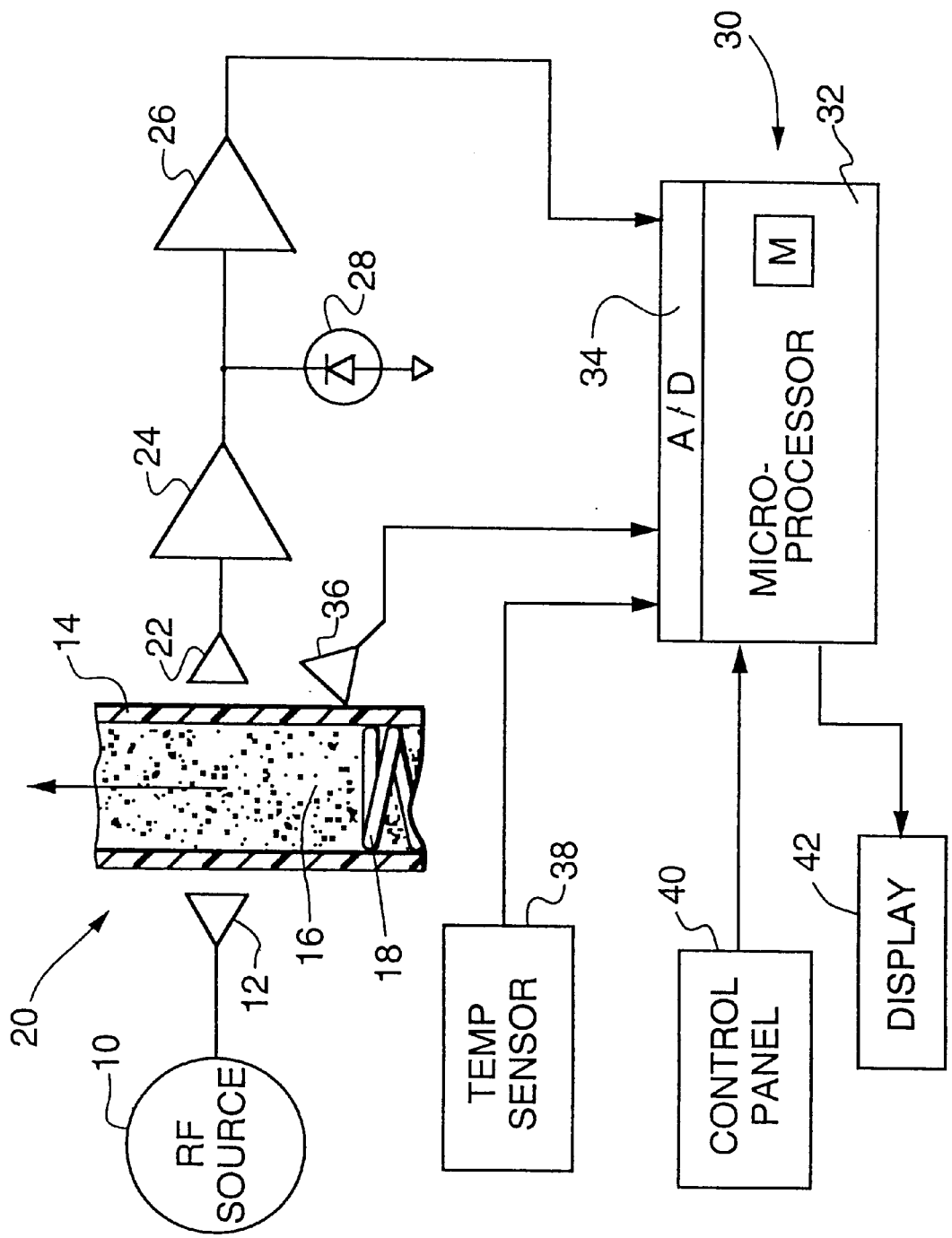
FIG. 1 is a schematic diagram illustrating a grain monitor and a sensing region defined by a portion of a grain feed tube of a harvesting machine.

As shown in FIG. 1, a grain monitor constructed in accordance with the principles of the present invention comprises a source 10 producing a continuous wave RF signal of approximately 200 mW at a frequency of about 2.5 GHz. The power and frequency may vary but preferably the frequency is at least one GHz. RF source 10 is coupled to a transmit antenna 12 disposed on one side of a sensing region 20. Source 10 and antenna 12 comprise a means for transmitting a microwave measurement signal through the sensing region.

The grain feed tube 14 of a harvesting machine extends upwardly through the sensing region 20 and grain 16 is pushed upwardly through the tube 14 and sensing region by a grain auger 18. Because the grain 16 is pushed upwardly against gravity, the packing density of the grain is uniform throughout the sensing region 20 and the grain density depends on the moisture content of the grain.

A receive antenna 22 is disposed adjacent the grain tube 14 on the opposite side of the sensing region 20 from the transmit antenna 12. The receive antenna is coupled to an RF preamplifier 24 which in turn is connected to an RF power detector diode 28 and an operational amplifier 26. In an operative embodiment, antenna 22, like antenna 12, had a gain of 3 dB, and preamplifier 24 had a gain of approximately 30 dB.

Antenna 22, diode 28 and amplifiers 24 and 26 comprise a means for detecting the magnitude of the measurement signal after it has passed through the sensing region and has been attenuated by moisture contained in the grain 16. Amplifier 24 amplifies the small signal picked up by antenna 22. The detector diode 28 is used to rectify the received continuous wave RF and to provide increased dynamic range of this signal by allowing the strongest signals to drive the diode into saturation. This provides a low signal region of linear detection for high moisture grain measurements and a non-linear high signal range for low moisture grain. The high signal range is needed for the driest grains with the least attenuation (essentially 0 dB, with a worst case high moisture of 6 dB per cm). The detected signal is then amplified in operational amplifier 26 to a level which utilizes the full dynamic range of an analog to digital converter 34 to which the output of amplifier 26 is connected.

A/D converter 34 has multiplexed inputs connected to a microwave Doppler transceiver 36 antenna and a temperature sensor 38 as well as the output of amplifier 26. The transceiver antenna 36 is disposed at an angle, preferably 45°, relative to the direction of grain flow and serves to detect the velocity or rate of flow of grain particles through the sensing region 20. The purpose of temperature sensor 38 is to provide an indication of the temperature of the grain in the sensing region. The sensor senses ambient temperature and preferably is disposed near the sensing region 20.

A/D converter 34 is part of a programmable controller 30 which further comprises a conventional microprocessor 32 and a memory means M. The memory means M includes conventional read/write and ROM storage and a Flash EEPROM or other nonvolatile memory for storing grain density coefficients as subsequently described.

In recent years, harvesters have been provided with an operator's key pad control panel 40 with keys or push buttons and an associated display 42 for entering data and control information and displaying various messages regarding the status of the harvester. The control panel 40 is utilized in the present invention to load grain density coefficients into memory M, one set of coefficients being loaded for each type of grain it is expected will be harvested. New sets of coefficients may be added when new types of grain are to be harvested. The control panel is also utilized at the start of each harvesting operation to select for use the set of grain coefficients corresponding to the type of grain to be harvested.

The display 42 is utilized in the present invention to display numerical values representing the moisture content of grain passing through sensing region 20, the volume flow of grain through the grain tube 14, the grain density and the mass flow.

Although FIG. 1 illustrates the control panel 40 and display 42 as being connected directly to microprocessor 32, in actual practice these elements may be connected to another microprocessor (not shown) in the harvester which is in turn networked with microprocessor 32 via a conventional link such as a CAN network.

Figure 2:
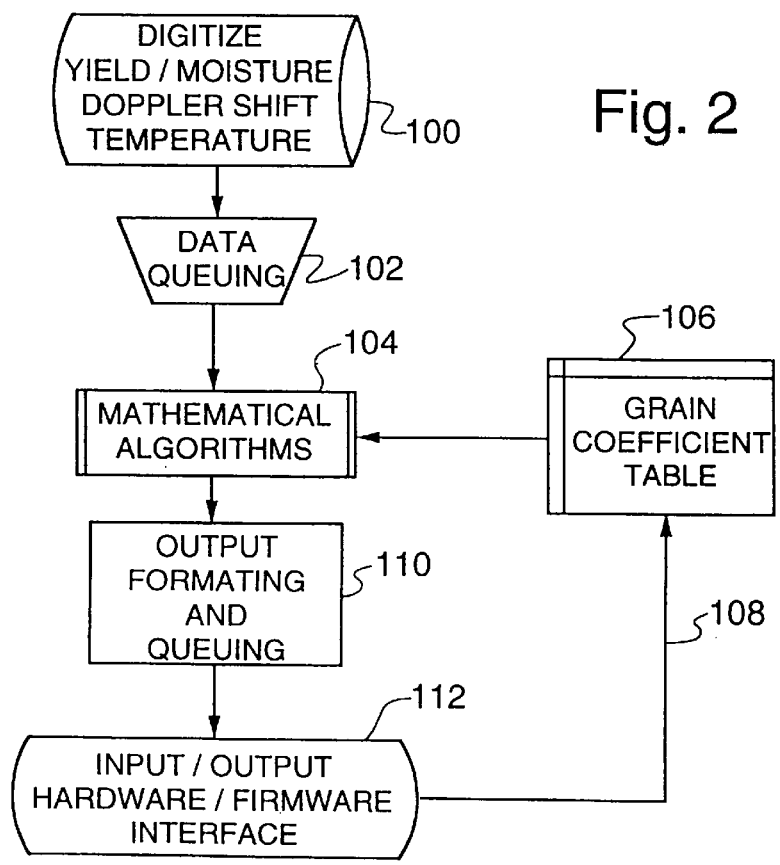
FIG. 2 is a flow diagram illustrating the sequence of operations performed by the microprocessor of FIG. 1 in determining grain moisture content and mass flow; and, FIG. 3 is a flow diagram illustrating the mathematical algorithm performed by the microprocessor.

FIG. 2 illustrates in a general manner the operations or steps performed by the controller 30 operating according to a program stored in the ROM portion of memory M. Step 100 gathers the sensor data. The real time capture of the analog sensor data is driven by a 500 Hz periodic interrupt generated by a timer in microprocessor 32. A/D converter 34 is controlled to sample and digitize the analog signal from Doppler transceiver 36 at a rate of 500 times per second. The yield/moisture (RF attenuation) output signal from amplifier 26 is sampled and digitized 100 times per second. The analog output signal from temperature sensor 38 is sampled and digitized once each second. These sampling rates are nominal and other sampling rates may be used.

Data queuing takes place at step 102. The digitized data from the various sensors is double buffered. That is, first and second buffers or sets of locations in memory M are designated for storage of the digitized data derived from amplifier 26, temperature sensor 38 and transceiver 36. Every other time the signal from one of these sources is digitized, the digitized value is stored at a location in the first buffer, and the next time the signal from the same source is digitized the digitized value is stored at a location in the second buffer. While data is being loaded into the first buffer, the data in the second buffer is used for computation of moisture content, yield, etc., and while data is being loaded into the second buffer the data in the first buffer is used for the computation. A buffer pointer or flag is generated to keep track of whether the first or second buffer is being loaded. This flag is passed to a routine which performs the computations so that the routine will know what data to use. The purpose of the double data buffering is to improve the reliability of the real time data gathering.

At step 104, microprocessor 32 calculates the moisture content, grain flow, etc. A suitable mathematical algorithm for accomplishing this is described below. In executing step 104, the microprocessor determines from the state of the previously mentioned buffer flag which buffer holds the data to be used in the computations. The computations require the use of grain density coefficients which differ according to the type of grain. A table of grain density coefficients, indicated at 106, is stored in memory M. These coefficients are experimentally determined and loaded into table 106 at any time prior to the start of a harvesting operation. The density coefficients for some grain types may be loaded at the factory or at a dealership and the coefficients for other grain types may be added as needed. As previously indicated, the density coefficients are loaded via control pane 40 and this is indicated in FIG. 2 by the line 108.

Prior to beginning a harvesting operation, an operator enters into microprocessor 32, via control panel 40, an indication of the type of grain to be harvested. During execution of step 104, the microprocessor uses this indication to select the appropriate set of density coefficients from the coefficient table 106.

Steps 110 and 112 are required only if the microprocessor 32 is connected to control panel 40 and display 42 via a network as previously mentioned. Step 110 calls I/O interface routines from a CAN bus library. These routines are conventional and handle the building of CAN messages of up to 8 bytes and the passing of these messages to interrupt-driven CAN bus I/O hardware and firmware. These messages contain the results of the computations performed at step 104. At step 112, the I/O hardware and firmware transmits queues of messages passed to it from step 110. These messages are transmitted to the microprocessor (not shown) to which the control panel 40 and display 42 are connected. Keys or buttons on control panel 40 may be operated to select which of the computation results is displayed on the display 42.

In the case where the grain monitor processor 32 is not networked, the results of the computations carried out at step 104 may be entered into registers and selected for display by operation of the keys or buttons on the control panel 40.

Figure 3:
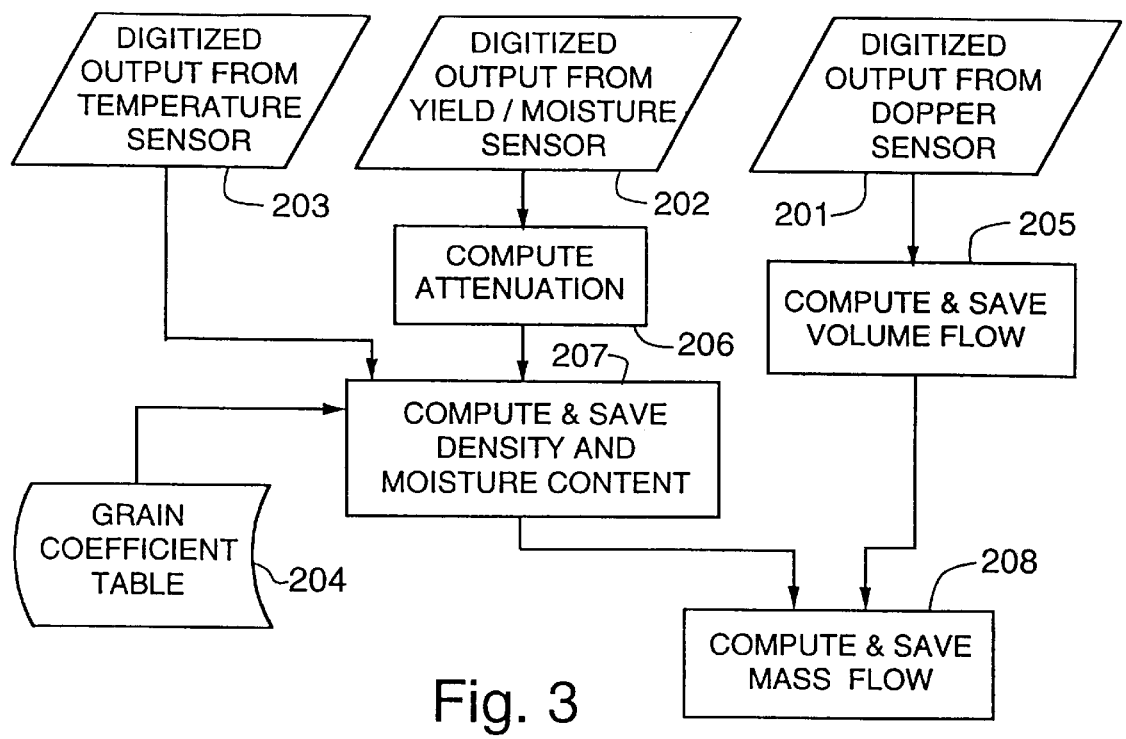

FIG. 3 illustrates the sequence of operations performed by microprocessor 32 to calculate the grain moisture content, volume flow, mass flow and grain density. The input data required for these calculations includes the digitized outputs from the Doppler sensor 36, the yield/monitor sensor amplifier 26 and the temperature sensor 38, these inputs being represented at 201, 202 and 203, respectively, in FIG. 3. Two additional inputs are required. These are the buffer pointer or flag which selects the sensor data from the appropriate one of two buffers, as previously explained, and an indication of the type of grain being harvested. The grain type is entered into microprocessor 32 prior to the start of the harvesting operation and used during the calculation of moisture content and density to select the appropriate set of grain coefficients from the grain coefficient table indicated at 204.

The digitized output of Doppler sensor 36 is selected from the appropriate buffer and used to calculate the volume flow. Step 205 first analyzes the digitized output to determine the frequency shift, that is, the difference in frequency between the signal transmitted and the signal received by sensor 36. From the frequency shift, the velocity V of the grain is determined where $V = \lambda/2\cos\theta f_d$ $\lambda$=wavelength of transmitted signal $\theta$=angle between transmitter and direction of grain flow $f_d$=difference between transmitted and received frequencies Memory M permanently stores a constant value corresponding to the internal cross-sectional area of the grain feed tube 14. Step 205 multiplies the computed grain velocity V by this value to obtain the volume flow of grain. The volume flow, in bushels per minute or equivalent units, is saved in a register in memory M and may be displayed on the display 42 by operation of push buttons on control panel 40.

The digitized output from the yield/moisture sensor is used at step 206 to compute the attenuation. The digitized output of amplifier 26 is averaged over a one-second interval. The average value is converted to decibels (dB=20 log A) by a combination of table look-up and calculation. The value in decibels is then subtracted from a calibration value previously stored in memory and obtained by determining the attenuation when sensing region 20 is empty, that is, has no grain therein.

The computed attenuation and the digitized output from temperature sensor 38 are utilized to compute the grain moisture content as indicated 207. These computations require the grain coefficients stored in the grain coefficient table. The grain type, entered into the microprocessor prior to the start of the harvesting operation, is retrieved and used to access the appropriate set of grain coefficients in the coefficient table.

A set of grain coefficients comprises the wet grain coefficients $\alpha_w$, $\gamma_w$, $\delta_w$ and $T_{0w}$, and the dry grain coefficients $\alpha_d$, $\beta_d$, $\gamma_d$, $\delta_d$ and $T_{0d}$, where $T_{0w}$ is the temperature at which the other wet grain coefficients are determined and $T_{0d}$ is the temperature at which the other dry grain coefficients are determined. The grain coefficients are experimentally determined for each type of grain by directing a microwave signal having a frequency equal to that of source 10 through a plurality of samples with different moisture contents packed to a density substantially equal to the density resulting from pushing the grain upwardly in a confining tube. The attenuation of the signals are measured and the coefficients selected to satisfy equation (1)–(4) set forth below. The coefficients are then entered into the coefficient table via control panel 40.

The calculation of grain moisture content and grain density is carried out by first calculating two temperature correction factors $Tcomp_w$ and $Tcomp_d$ according to the equations:

$$Tcomp_w = \gamma_w(\delta_w{}^{log\,(T_{0w}-T)}) \text{ if } T<T_{0w} \qquad (1)$$

$Tcomp_w = 0$ if $T \leq T_{0w}$ $$Tcomp_d = \gamma_d(\delta_d{}^{log\,(T_{0d}-T)}) \text{ if } T<T_{0d} \qquad (2)$$

$Tcomp_d = 0$ if $T \leq T_{0d}$ where T is the grain temperature as sensed by temperature sensor 38.

Next, step 207 determines two mass densities $D_w$ and $D_d$, where $D_w$ is the mass density (g/cc) of water in the sample and $D_d$ is the mass density (g/cc) of other material in the sample. The wet and dry densities are determined according to the equations:

$$D_w = \alpha_w + \beta_w \log(\text{atten}) + T\text{comp}_w \quad (3)$$

$$D_d = \alpha_d + \beta_d \log(\text{atten}) + T\text{comp}_d \quad (4)$$

The total density $D_t$ is the sum of the wet and dry densities $D_d$ and $D_w$ and the grain moisture content MC is computed by dividing the wet density $D_w$ by the total density $D_t$. The computed moisture content in units of percent by mass or equivalent, and the computed mass density of the grain in units of g/cc or equivalent are saved in memory and may be selectively called for display on the display 42 by operation of keys on the control panel 40.

The mass density of the grain determined at step 207 and the volume flow determined at step 205 are multiplied at step 208 to obtain the mass flow of the grain. The product is converted to appropriate units of kilograms per minute or equivalent and saved in memory M so that it may be selected for display by operation of the control panel keys.

From the foregoing description it is seen that the invention provides a microwave grain monitor capable of determining grain moisture content by measuring attenuation without concurrent measurement of phase shift. The impact of eliminating the phase measurement on the accuracy, cost and complexity of sensor design is significant. In the paper referenced above, a typical attenuation and phase measurement system is outlined. The radio frequency detector to measure phase and amplitude is readily available as a quadrature detector. The quadrature detector produces two outputs displaced in time from each other by 90 degrees. These two signals (in-phase (I) and quadrature (Q)) are processed in the electronics by taking the tangent of the ratio of the two outputs I and Q. The magnitude of the attenuation is produced by squaring the two outputs, adding them together and taking the square-root. A representative low cost quadrature detector for this purpose at 10 GHz is relatively expensive.

According to the present invention, the consistent packing of the grain in the grain feed tube means that only the attenuation need be measured since under consistent packing conditions the moisture content and bulk density are functionally related for each grain type. Measurement of only the attenuation significantly impacts the cost of the sensor by replacing the quadrature detection and associated signal processing with an amplitude detector diode.

In addition, the use of an amplitude measurement does not require reference power from the radio frequency source (transmitter) for purposes of comparison. As a result, more power is available to the transmit antenna and an improvement in received signal-to-noise ratio results over the I and Q method. The detector diode measures the received radio frequency power after passing through the flowing grain under test. The difference between the transmitted radio frequency power and the received power is the power lost to absorption in the grain moisture. The normalized power loss over the grain path length then is compared to known loss values for the particular grain at known moisture contents.

It is obvious that the invention not only is less expensive to construct, but requires much less complexity in evaluation and signal processing of the received radio frequency signals by the microprocessor to determine the moisture content and bulk density of the tested grain.

Although a preferred embodiment has been described in detail to illustrate the principles of the invention, it will be understood that various modifications and substitutions may be made in the described embodiment without departing from the spirit and scope of the invention as defined by the appended claims.

We claim:

1. A method of determining the moisture content of grain, said method comprising the steps of:

(a) forming the grain into a packed mass of grain having a consistent particle density and moving the grain through a sensing region;

(b) establishing by experiment a set of grain coefficients relating to grain of the type moved through the sensing region;

(c) directing a microwave measurement signal through the grain in the sensing region while measuring the ambient temperature;

(d) determining the attenuation (atten) of the measurement signal in passing through the grain;

(e) calculating the wet density $D_w$ and the dry density $D_d$ from the sensed temperature, the determined attenuation and the set of grain coefficients; and (f) calculating the moisture content from the wet density and the dry density.

2. A method as claimed in claim 1, wherein step (a) comprises confining the grain in a conveying tube extending through the sensing region.

3. A method as claimed in claim 2, wherein the consistent particle density is obtained by pushing the grain through the conveying tube.

4. A method as claimed in claim 3, wherein the conveying tube is oriented vertically and the grain is pushed against gravity to obtain the consistent packing density.

5. A method as claimed in claim 1, wherein step (b) comprises establishing a set of wet grain coefficients and a set of dry grain coefficients at temperatures $T_{ow}$ and $T_{od}$, respectively.

6. A method as claimed in claim 1, wherein step (b) comprises establishing a set of wet grain coefficients $\alpha_w$ and $\beta_w$ and a set of dry grain coefficients $\alpha_d$ and $\beta_D$ at temperatures $T_{ow}$ and $T_{od}$, respectively, and step (e) comprises calculating the wet density $D_w$ and the dry density $D_d$ according to the equations $$D_w = \alpha_w + \beta_w \log(\text{atten}) + T\text{comp}_w$$

$$D_d = \alpha_d + \beta_d \log(\text{atten}) + T\text{comp}_d$$

where (atten) is the attenuation of the measurement signal in passing through the sensing region and $T\text{comp}_w$ and $T\text{comp}_d$ are temperature correction factors derived from $T_{od}$, $T_{ow}$ and the measured ambient temperature.

7. A method as claimed in claim 1, wherein step (b) comprises directing a microwave signal having frequency equal to that of the microwave measurement signal through a plurality of samples of grain packed to the same particle density as said consistent particle density.

8. A method of determining the moisture content of grain as the grain is pushed upwardly through a feed tube extending through a sensing region, said method comprising:

(a) establishing by experiment a set of grain coefficients relating to grain of the type pushed through the feed tube;

(b) directing a microwave measurement signal through the grain in the sensing region while measuring the ambient temperature;

(c) determining the attenuation of the measurement signal in passing through the grain;

(d) calculating the wet density $D_w$ and the dry density $D_d$ from the sensed temperature, the determined attenuation and the set of grain coefficients; and, (e) calculating the moisture content from the wet density and the dry density.

* * * * *